US006811967B2

(12) United States Patent
Sitar et al.

(10) Patent No.: US 6,811,967 B2
(45) Date of Patent: Nov. 2, 2004

(54) METHOD FOR ASSAYING NON-SPERMINE/SPERMIDINE ACTIVITY OF SPERMIDINE/SPERMINE $N^1$-ACETYLTRANSFERASE (SSAT)

(75) Inventors: Daneil S. Sitar, Winnepeg (CA); Alvaro P. M. Bras, Winnipeg (CA)

(73) Assignee: The University of Manitoba, Winnipeg (CA)

( * ) Notice: Subject to any disclaimer, the term of this patent is extended or adjusted under 35 U.S.C. 154(b) by 0 days.

(21) Appl. No.: 10/085,051

(22) Filed: Mar. 1, 2002

(65) Prior Publication Data

US 2002/0132280 A1 Sep. 19, 2002

Related U.S. Application Data

(60) Provisional application No. 60/272,322, filed on Mar. 2, 2001.

(51) Int. Cl.$^7$ .......................... C12Q 1/00; G01N 33/567
(52) U.S. Cl. .......................................... 435/4; 435/7.21
(58) Field of Search ..................................... 435/4, 7.21

(56) References Cited

PUBLICATIONS

Diane H. Russell, Nature New Biology, vol. 233, (Sep. 29, 1971), pp. 144–145.
Martin J. Pine et al., The Journal of Urology, vol. 141, (1989), pp. 651–655.
Marko Pietila et al., The Journal of Biological Chemistry, vol. 272, No. 30, (Jul. 25, 1997), pp. 18746–18751.
Anthony E. Pegg et al., Biochimica et Biophysica Acta, vol. 1171, (1992), pp. 106–108.
Anthony E. Pegg et al., Federation Proceedings, vol. 41, (1982), pp. 3065–3072.
Lisa Parry et al., Biochem. Journal, vol. 305, (1995), pp. 451–458.
Yanlin Wang et al., The Journal of Biological Chemistry, vol. 273, No. 51, (Dec. 18, 1998), pp. 34623–34630.
Yanlin Wang et al., The Journal of Biological Chemistry, vol. 274, No. 31, (Jul. 30, 1999), pp. 22095–22101.
Yanlin Wang et al., Biochemical Journal, vol. 355, No. 1, (2001), pp. 45–59.
Robert H. Tannen et al., Drug Metabolism and Disposition, vol. 7, (1979), pp. 274–279.
Seiichi Takenoshita et al., Cancer Research, vol. 44, (Feb. 1984), pp. 845–847.
Ja Won Suh et al., Journal of Chromatography B, vol. 688, (1997), pp. 179–186.
D.S. Sitar et al., Clin. Pharmacol. Ther., vol. 49.2, (PII–29), (1991), pp. 156.
A. Sessa et al., Cancer Letters, vol. 56, (1991), pp. 159–163.
Nikolaus Seiler et al., Biochimica et Biophysica Acta, vol. 354, (1974), pp. 206–212.
Nikolaus Seiler, Can. J. Physiol. Pharmacol., vol. 65, (1987), pp. 2024–2035.

Mirjana Fogel–Petrovic et al., Molecular Pharmacology, vol. 52, 1997, pp. 69–74.
Kerry B Goralski et al. The Journal of Pharmacology and Experimental Therapeutics, vol. 290, No. 2, (1999), pp. 496–504.
Dean Hickman et al., Biochemical Pharmacology, vol. 50, No. 5, (1995), pp. 697–703.
A.N. Kingsnorth et al., Eur. J. Cancer Clin. Oncol., vol. 21, No. 9, (1985), pp. 1057–1062.
Claus Koppel et al., Biomedical Mass Spectrometery, vol. 12, No. 9, (1985), pp. 499–501.
Isao Matsui et al., Biochimica et Biophysica Acta, vol. 633, (1980), pp. 87–94.
Isao Matsui et al., Biochemical and Biophysical Research Communications, vol. 92, No. 3, (Feb. 12, 1980), pp. 1009–1015.
Isao Matsui et al., The Journal of Biological Chemistry, vol. 256, No. 6, (Mar. 10, 1981), pp. 2454–2459.
David M.L. Morgan, Methods in Molecular Biology, vol. 79, pp. 3–30., 1997.
Lei Xiao et al., Biochemical and Biophysical Research Communications, vol. 187, No. 3, (Sep. 30, 1992), pp. 1493–1502.
Herbert H. Andres et al., Drug Metabolism and Disposition, vol. 14, No. 4, (1986), pp. 382–385.
Saverio Bettuzzi et al., Cancer Research, vol. 60, (Jan. 1, 2000), pp. 28–34.
Jim Blankenship et al., Archives of Biochemistry and Biophysics, vol. 179, (1977), pp. 235–242.
W.E. Bleidner et al., The Journal of Pharmacology and Experimental Therapeutics, vol. 150, No. 3, (1965), pp. 484–490.
Alvaro P.M. Bras et al., Can. J. Physiol. Pharmacol., vol. 76, (1998), pp. 701–706.
Robert A. Casero, Jr. et al., The FASEB Journal, vol. 7, (May 1993), pp. 653–661.
S.S. Cohen, A Guide to the Polymines, (1998), pp. 193–319.

(List continued on next page.)

Primary Examiner—Jon P. Weber
Assistant Examiner—Kailash C. Srivastava
(74) Attorney, Agent, or Firm—Birch, Stewart, Kolasch & Birch LLP

(57) ABSTRACT

This invention relates to a method for assaying activity of the enzyme spermidine/spermine $N^1$-acetyltransferase (SSAT) using SSAT substrates by detecting acetylated forms of the SSAT substrates. SSAT substrates may include amantadine wherein metabolism of amantadine occurs in part by the action of the inducible enzyme SSAT to produce the acetylated metabolite N-acetylamantadine.

10 Claims, 5 Drawing Sheets

OTHER PUBLICATIONS

W.L. Davies, et al., Science, vol. 144, (1964), pp. 862–863.

Jean–Marie Dupret et al., The Journal of Biological Chemistry, vol. 267, No. 11 (1992), pp. 7381–7385.

M. Fogel–Petrovic et al., Biochimica et Biophysica Acta, vol. 1216, (1993), pp. 255–264.

G.W. Haywood et al., "The occurrence, subcellular localization and partial purification of diamine acetyltransferase in the yeast *Candida boidinii* grown on spermidine or putrescine as sole nitrogen source", European Journal of Biochemistry, vol. 148, No. 2, 1985, pp. 277–284.

R.F. Della et al., Abstract of "Studies of the specificity and kinetics of rat liver spermidine spermine N–1 Acetyl trans ferase", Biochemical Journal, vol. 213, No. 3, 1983, pp. 701–706, Database Biosis XP–002264589.

A.P.M. Bras et al., "Spermidine/Spermine $N^1$–Acetyltransferase Catalyzes Amantadine Acetylation", Drug Metabolism and Disposition, vol. 29, No. 5, 2001, pp. 676–680.

METHOD FOR ASSAYING NON-SPERMINE/SPERMIDINE ACTIVITY OF SPERMIDINE/SPERMINE N$^1$-ACETYLTRANSFERASE (SSAT)

This application claims priority on Provisional Application No. 60/272,322 filed on Mar. 2, 2001, the entire contents of which are hereby incorporated by reference.

FIELD OF THE INVENTION

This invention relates to a method for assaying activity of the enzyme spermidine/spermine N$^1$-acetyltransferase (SSAT) using SSAT substrates by detecting acetylated forms of the SSAT substrates. SSAT substrates may include amantadine wherein metabolism of amantadine occurs in part by the action of the inducible enzyme SSAT to produce the acetylated metabolite N-acetylamantadine.

BACKGROUND OF THE INVENTION

Amantadine was first synthesized at the Du Pont laboratories in the 1960s (Davies et at., 1964) and has a unique polycyclic aliphatic structure, with an achiral primary amine that makes it a weak base (pKa=10.1). At physiological pH, it exists mainly in the cationic form. Amantadine has been used as an adjunct in the symptomatic relief of Parkinson's disease and for the prophylaxis and treatment of influenza A virus infection the two approved clinical indications for amantadine in Canada.

The first report that addressed amantadine metabolism was by Bleidner et al. They stated that there was no evidence of acetylated or methylated forms of amantadine in human urine or other extraneous peaks that could be attributed to metabolites of the drug (Bleidner et al., 1965). This view was accepted and formed the basis of opinion concerning amantadine metabolism and the assumption that incomplete oral absorption could account for some of the unrecovered dose. More recently evidence indicates that amantadine is acetylated by a specific acetyltransferase.

Amantadine Metabolism

Koppel and Tenczer (1985) provided the first evidence for metabolic disposition of amantadine in humans. These researchers reported that 5 to 15% of the administered dose (200 mg) was recovered in the urine as acetylamantadine in three healthy young male volunteers. Furthermore, they reported the existence of other minor metabolites, which were not quantified. They suggested that other minor metabolic pathways may be involved in N-methylation, formation of Schiff bases and N-formiates. There was no evidence for oxidation of the adamantane ring (Koppel & Tenczer, 1985). This observation was extended by Sitar et al., when they reported that acetylation of amantadine was not correlated with the N-acetyltransferase 2(NAT2) acetylator phenotype This observation suggested that NAT2 was not the acetyltransferase enzyme that catalyzed this conjugation reaction (Sitar et al., 1991). Further still, Bras et al. (1998) reported amantadine acetylation may be effected by acetyltransferases other than N-acetyltransferase 1 (NAT1) or NAT 2.

Spermidine/Spermine Acetyltransferase (SSAT)

Spermidine/spermine N$^1$-acetyltransferase (SSAT), is ubiquitously distributed in mammalian issues and plays a role in catabolism and elimination of polyamines from cells (Cohen; 1998; (Morgan, 1998). However, in normal or uninduced mammalian tissues SSAT is present at very low levels (Casero & Pegg, 1993; Cohen, 1998). SSAT is an inducible enzyme that catalyzes the transfer of an acetyl group from acetyl-coenzyme A to the aminopropyl moiety of polyamines. This action by SSAT facilitates polyamine degradation, excretion, cycling and/or intracellular cycling (Casero & Pegg, 1993). In this manner SSAT participates in the maintenance of polyamine homeostasis in mammalian cells.

Regulation of SSAT

Induction of SSAT can be caused by different drugs, growth factors, polyamines, polyamine analogues, toxic substances, hormones, and physiological stimuli (Casero & Pegg, 1993). All could cause induction, but the induction occurs at different times for each individual compound. The regulation of SSAT expression occurs at the levels of transcription, mRNA stability, mRNA translation and protein stability (Fogel-Petrovic; et al., 1997).

The SSAT gene contains a polyamine responsive element located in a region that occurs at −1522 to −1492 with respect to the SSAT transcriptional start site (Wang et al., 1998). Within this 31 base pair sequence, the polyamine response element was identified as a 9 base pair sequence. The polyamine response element mediates transcriptional induction of SSAT by the polyamine analogue N$^1$,N$^{12}$-bis (ethyl)spermine or natural polyamines (Wang et al., 1998).

SSAT, the rate-limiting enzyme in the catabolic pathway plays a regulatory role in maintaining spermidine and spermine homeostasis. It has been estimated that less than 1000 molecules of SSAT are present in a rat hepatocyte, compared to 60,000 molecules in an induced cell (Matsui & Pegg, 1981; Pegg et al., 1982). The induction of mammalian tissues by the various inducers can result in increased levels of SSAT that in turn may serve as a potential acetylator of primary amine-containing compounds.

Induction or over-expression of SSAT is usually required for there to be sufficient SSAT enzyme present in cells or 100,000×g supernatant before in vitro experiments can be successfully undertaken (Casero & Pegg, 1993; Fogel-Petrovic et al., 1997; Matsui & Pegg, 1980; Pietila et al., 1997).

Thus, while the literature teaches that SSAT is an acetylating enzyme specifically for substrates including spermine and spermidine or its analogues, SSAT activity, SSAT enzyme kinetics and assay methodology for non-spermine/spermidine substrates of SSAT has not been understood. Current methods exist to quantitate SSAT activity however these techniques are dependent on highly skilled personnel and involve complicated experimental methods. More specifically, there has been a need for assay methodology which quantifies the activity of SSAT through detection of acetylated forms of non-spermine/spermidine substrates of SSAT, including amantadine which may be used to detect various pathological conditions.

SUMMARY OF THE INVENTION

In accordance with the invention, there is provided a method for determining the activity of spermine/spermidine N$^1$-acetyltransferase (SSAT) in a mammal comprising the step of assaying a sample derived from the mammal for the level of an acetylated form of a non-spermine/spermidine, (or analogues thereof), SSAT substrate in the sample.

In one embodiment, the SSAT substrate is amantadine and the acetylated form of an SSAT substrate is acetylamantadine. The method may include incubating the SSAT substrate with the mammal or mammalian tissue or cells at a specific SSAT substrate dosage level, preferably in the range of 1–4 mg/kg and more preferably at 3 mg/kg. Samples to be assayed may be urine and/or blood samples from the mammal which may be collected at 2–24 following substrate incubation and preferably at 8 hours following incubation.

The relative level of the non-spermine/spermidine SSAT substrate in the sample is preferably correlated to a standard curve representing known activity levels and may be assayed by a variety of techniques including but not limited to gas chromatography, radio-labelling, mass spectrometry, high performance liquid chromatography (HPLC) and thin-layer chromotography.

In another embodiment of the invention, the assay method is used to correlate SSAT activity to pathological conditions in the mammal including gastric carcinoma, ovarian cancer, acute myelocytic leukemia, lymphoma, breast cancer, renal cancer, colorectal cancer, prostate cancer or alcohol consumption.

BRIEF DESCRIPTION OF THE DRAWINGS

The invention is described with reference to the drawings wherein.

DETAILED DESCRIPTION OF THE INVENTION

Figure 1:
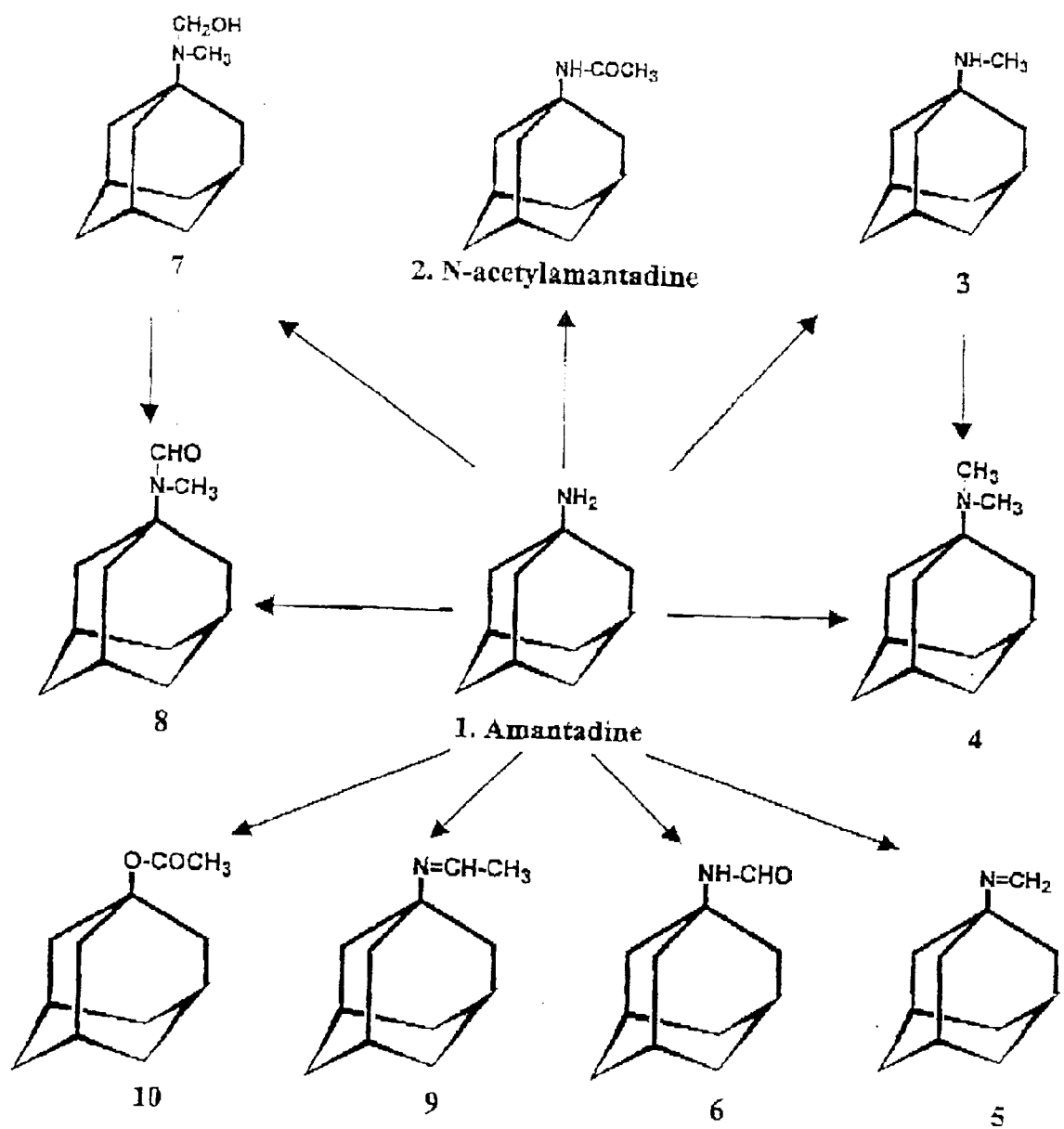
FIG. 1 represents the metabolic disposition of amantadine (Adapted from Köppel and Tenczer (1985)) 1. Amantadine 2. N-Acetylamantadine (major metabolite) 3. N-methylamantadine 4. N,N$^1$-dimethylamantadine 5. N-methyleneamantadine 6. N-formylamantadine 7. and 8. possible stepwise oxidation of N-dimethylamantadine (4) 9. N-ethylideneamantadine 10. 1-adamantol acetate.

In accordance with the invention and with reference to the Figures, a method for assaying SSAT activity is described for in vitro and in vivo models.

Experiments

Experiments to determine if SSAT is an enzyme responsible for the acetylation of amantadine were undertaken.
Transgenic Animal Studies CD2F1 transgenic mice overexpressing spermidine/spermine N$^1$-acetyltransferase were generated at the A. I. Virtanen Institute for Molecular Sciences (University of Kuopio, Kuopio, Finland). The transgene construct for these mice was from a genomic sequence isolated 129 SVJ mouse genomic library as previously described (Marko Pietilä et al., 1997). The transgenic mice were propagated and maintained at the Grace Cancer Drug Center (Roswell Park Cancer Institute, Buffalo, N.Y.). CD2F1 non-transgenic mice were obtained from Charles River Laboratories (St. Constant, Quebec, Canada).
In Vivo Experiments Both transgenic and non-transgenic CD2F1 mice were injected subcutaneously with a dose of 3 mg/kg amantadine HCl (0.5 mg/ml). The stock amantadine for injection was prepared by dissolving amantadine HCl in normal saline for injection. The solution was then filtered into a sterile vial using a 0.22$\mu$ GV Millex filter (Millipore Canada, Mississauga, Ontario) and stored at 4° C. The mice were placed in separate metabolic cages. The total urine was collected and washed from the sides of the metabolic cages with DDW at 3, 6, 9 and 24 hr after drug injection. The urine was frozen at −20° C. until analyzed for acetylamantadine.
Modified Gas-Liquid Chromatography Acetylamantadine was quantified by gas-liquid chromatography as previously described (Bras et al., 1998), and modified to improve sensitivity. The modified procedures used solid phase extraction as follows: Supelclean™ ENVI™-18 SPE tubes, 3 ml (Supelco, Bellafonte, Pa.) were primed with 2 ml of methanol, and 2 ml of DDW, followed by 2 ml of 0.2 M sodium phosphate buffer pH 7.4. The mouse urine samples of 1.0 ml were mixed with 50 $\mu$l acetanilid (5 mg/l, dissolved in DDW), as an internal standard and 1.0 ml of buffer. The samples were loaded on the columns and allowed to permeate. The columns were washed with 2 ml 0.2 M sodium phosphate buffer followed by two washes of 2.5 ml DDW. Excess water was removed under low vacuum pressure. The column was eluted with 2 ml ethyl acetate to extract acetylamantadine and internal standard, and evaporated under a stream of nitrogen to dryness in a fume hood at room temperature. The residue was reconstituted with toluene (35 $\mu$l), allowed to stand for 30 min, and mixed for 2 min. Samples (1 $\mu$l) from the reconstituted residue were injected into an Hewlett Packard model 5890 series II gas chromatograph using helium as the carrier gas and a Hewlett Packard high performance (crossed-linked methyl silicone gum) 25 m×0.2 mm×0.3 $\mu$m film thickness capillary column. The detector temperature was 250° C., injection port 250° C., and oven temperature was programmed so that the initial temperature was 150° C. for 2 min, then increased by 10° C./min to 200° C. and held for 1 min, increased by 70° C./min up to 240° C. and held for 15 min. A nitrogen-specific detector was used.

Standard curves for acetylamantadine were derived from blank urine (diluted 1:10) with DDW or plasma (for sub-cellular metabolism studies) to which known amounts of acetylamantadine were added. The concentration range of the calibration curves for both urine and plasma was from 6.25–800 ng/ml. Plasma and urine assays for the quantitation of acetylamantadine were performed in duplicate. Duplicates differing by more than 10% were reanalyzed. Urine samples outside of the calibration range were diluted and reanalyzed. In urine, $r^2$ was 0.99 and C.V.=10% (n=6). In plasma, $r^2$ was 0.98 and C.V=16% (n=3) over an 11 month period.

Other assay methods for measuring acetylamantadine levels can be incorporated as understood by those skilled in the art including radio labelling, mass spectrometry high performance liquid chromatography (HPLC) and thin layer chromatography.

Enzyme Preparation

Transgenic and non-transgenic male CD2F1 mice weighing 25 to 38 g were anaesthetized with pentobarbital sodium (200 mg/kg) injected intraperitoneally. A laparotomy was performed through which the mice were sacrificed by sectioning of the aorta, and the liver was removed immediately and placed in ice-cold Tris buffer containing 0.25 M sucrose, 50 mM Tris-HCl (pH 7.5 (pH adjusted using NaOH)), 25 mM KCl, 5 mM $MgCl_2$ and modified to include 1 mM EDTA, and 2.5 mM DTT to improve enzyme stability when homogenizing the liver. The liver was blotted, weighed, and finely minced with a tissue chopper (Mickle Lab. Engineering Co. Ltd., Gomshall, Surrey, UK.) at 4° C. The minced tissue was placed in two volumes of the Tris buffer and homogenized using a Polytron homogenizer (Kinematica GMBH, Lucerne, Switzerland) for 2 min at a power setting of 6. The homogenate was centrifuged at 100,000×g for 1 h at 4° C. (Beckman L8-80M automatic refrigerated ultracentrifuge, with T80 centrifuge Rotor) and the supernatant served as the source of spermidine/spermine $N^1$-acetyltransferase (SSAT). Supernatant protein was determined using the Biuret reagent method, as follows: 30 $\mu$l of supernatant was mixed with 120 $\mu$l of DDW and 600 $\mu$l of Biuret reagent, providing a five times dilution of the supernatant, and compared to a standard curve constructed using crystalline bovine serum albumin with a concentration range between 1 and 10 mg/ml. The colour was allowed to develop for 30 min and then read on a spectrophotometer at a wavelength of 540 nm (Pharmacia Biotech Ultraspec 4000, Pharmacia Biotech (Biochrom) Ltd., Milton Road, Cambridge, UK.). The dilution of the supernatant was necessary to prevent Tris homogenizing buffer from interfering with the Biuret assay. To confirm that no interference was occurring, an experiment was performed where the bovine serum albumin was mixed with either Tris homogenizing buffer or water to give the same protein concentration (10 mg/ml). The Tris buffer bovine serum albumin mixture was diluted 5× as described above and compared with albumin mixed with water after mixing with Biuret reagent and allowed to develop for 30 min. The results were identical for both (data not shown), indicating that this procedure provided results without interference from the Tris buffer.

Spermidine Acetylation Assay Procedures

The spermidine acetylation assays were completed by measuring the incorporation of radioactivity from [acetyl-1-$^{14}$C]-acetyl CoA as follows: tubes were prepared in triplicate by the addition of 20 $\mu$l spermidine dissolved in Tris-HCl buffer such that the concentrations in a final incubation volume of 100 $\mu$l were between 50 to 1000 $\mu$M for spermidine, and 100 mM Tris-HCl, pH 7.8 at 37° C. (pH adjusted with NaOH). A solution (20 $\mu$l) containing 40 nCi of [acetyl-1-$^{14}$C]-acetyl CoA dissolved in DDW was added to the tubes. The supernatant was adjusted with Tris buffer to give a protein concentration in the incubation medium of 1 mg/ml in a final incubation volume of 100 $\mu$l. Assay blanks were prepared in the absence of spermidine. The assay was initiated with the addition of 100,000×g supernatant (60 $\mu$) to the tubes and incubated for 10 min in a 37° C. water bath with shaking (80 oscillations/min) in a Haake SWB 20 incubator (Fisons Instruments, Haake Mess-Technik GmbH, Karlsrutte, Germany). The reaction was terminated by the addition of 20 $\mu$l of ice cold aqueous 1M hydroxylamine HCl; tubes were briefly mixed with a vortex-type mixer, and placed on ice. The reaction mixture was then placed in a boiling water bath for 3 min. The tubes were centrifuged at 12,000×g for 3 min to pellet the protein (Fisher Scientific Micro Centrifuge model 235c). An aliquot of the resultant incubation supernatant (50 $\mu$l) was applied and allowed to permeate 2.5 cm cellulose phosphate paper discs (Whatman, P-81, Whatman International Ltd., Maidstone, UK) that were previously wetted with DDW and placed on a vacuum box. Negative pressure was applied and the discs were washed 5 times with DDW, followed by three washes with 1.0 ml 95% v/v ethanol. The dried discs were placed into scintillation vials containing 4 ml of Ready Safe scintillation fluid (Beckman Coulter Inc., Fullerton, Calif.) and counted in a Beckman model LS6000TA scintillation counter (Beckman Instruments Inc., Fullerton, Calif.). To determine SSAT activity, the non-specific radioactivity of the blanks was subtracted from the total radioactivity of the samples containing the added spermidine.

Inhibition Studies

Inhibition of spermidine acetylation by SSAT was determined by the addition of amantadine, 1 to 10,000 $\mu$M, to fixed concentrations of spermidine, 50 to 80 $\mu$M. The NAT1 selective substrate PABA with a concentration range of 200, 500 and 1000 $\mu$M or the NAT2 selective substrate SMZ with range of 200, 500 and 700 $\mu$M were added to tubes containing spermidine (200 $\mu$M) and the acetylation reagents as described above. The PABA and SMZ were dissolved in 4% DMSO Tris-HCl buffer solution. The PABA and SWZ are first dissolved in 100% DMSO and then diluted using Tris-HCl buffer to the desired concentration of substrates; the final concentration of DMSO depended on the volume of buffer used for dilution. To ascertain that DMSO did not interfere with SSAT, two controls were run simultaneously, containing 200 $\mu$M spermidine dissolved in Tris-HCl buffer with and without DMSO. Spermidine acetylation was quantified as described above. All assays were performed in triplicate.

Amantadine Acetylation in Vitro Assay

Amantadine was incubated with transgenic mouse liver 100,000×g supernatant as the source of SSAT. An acetyl-CoA regenerating system was used as a source of acetate (Andres et al., 1985). The assay was performed in 1.5 ml microcentrifuge tubes. The assay buffer contained 225 mM Tris-HCl, 45 mM EDTA, and 4.5 mM DTT (pH 7.5 at 37° C.). In brief, 100 $\mu$l of acetyl-CoA (1 mM in DDW) and 100 $\mu$l of acetyl-CoA regenerating system (5.4 mg/ml acetyl-DL-carnitine HCl and 1 U/ml carnitine acetyltransferase dissolved in assay buffer) were added to the tubes. Then 200 $\mu$l of amantadine (50, 100, 200 $\mu$M) or a mixture of amantadine and SMZ (2500 $\mu$M) were dissolved in Tris-HCl buffer (pH 7.8) and added in manner such that the final incubation concentration of the buffer was 100 mM in the final volume of 1000 $\mu$l. To start the reaction, 600 $\mu$l of supernatant were added and incubated for 10 min at 37° C. The reaction was stopped by the addition of 200 $\mu$l of ice cold aqueous 1M hydroxylamine HCl and placed on ice. The protein was removed as previously described in the spermidine acetylation procedures section. The resultant incubation supernatant was frozen at −20° C. until analyzed for acetylamantadine using gas liquid chromatography.

Data Analysis

Data are expressed as mean±SE of at least three experiments. Apparent $K_m$ and $V_{max}$ values were determined by nonlinear regression fit to the Michaelis-Menten equation with the computer program (version 6.0a, Biososft, Ferguson, Mo.). $IC_{50}$ values for inhibition of spermidine acetylation were determined using regressive probit analysis graphical methods were used to assess the type of inhibition caused by amantadine. Urinary acetylamantadine excretion between transgenic mice was evaluated by the two-tailed Student's t test. Regression analysis was used to evaluate inhibitory activity of PABA and SMZ against spermidine acetylation. Differences between means with values $P \leq 0.05$ were considered significant. Analysis of variance (ANOVA) was used to detect significance among multiple groups.

Chemicals and Reagents

Sucrose, potassium chloride, dithiothreitol (DTT), magnesium chloride ($MgCl_2.6H_2O$), perchloric acid, glacial acetic acid, anhydrous dimethylsulfoxide, acetonitrile, and hydroxylamine HCl were acquired from Fisher Scientific, (Fisher Chemical, Fair Lawn, N.J.). Spermidine, Tris-HCl, EDTA, acetyl-coenzyme A (sodium salt), acetyl-DL-carnitine HCl, carnitine acetyltransferase (from pigeon breast muscle), sulfamethazine (SMZ), p-aminobenzoic acid (PABA), N-acetyl-p-aminobenzoic acid (AcPABA), triethanolamine-HCl, leupeptin, phenylmethysulfonyl fluoride, butylated hydroxytoluene, triethylamine, bovine serum albumin and methylglyoxal bis-(guanylhydrazone) (MGBG) were obtained from Sigma Chemical Company (St. Louis, Mo.) and [acetyl-1-$^{14}$C]-acetyl CoA (58.9 mCi/mmol) was purchased from New England Nuclear (Boston, Mass.). Amantadine HCl was provided by Dupont Canada Inc. (Mississauga, Ontario, Canada). Human albumin crystallized was purchased from Miles Scientific (Naperville, Ill.). N-acetyl-sulfamethazine (AcSMZ) was synthesized according to a previously published method (Svensson et al., 1991).

Results

Experiments Using Transgenic Mice Overexpressing SSAT

In Vivo Studies of Amantadine Acetylation.

Figure 2:
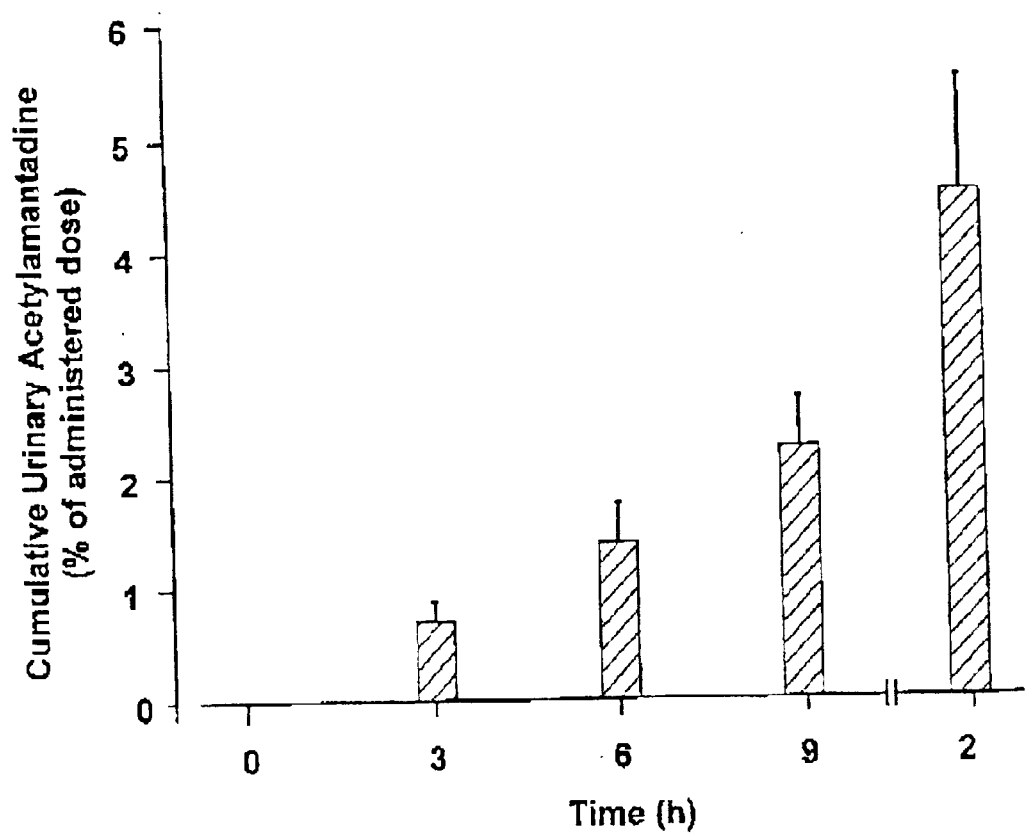
FIG. 2 is a plot of urinary excretion of acetylamantadine by transgenic mice overexpressing SSAT and injected with amantadine HCl (3 mg/kg). Control non-transgenic mice undergoing the same procedures did not excrete acetylamantadine in their urine. The values reported are mean±S.E. of 4 separate experiments.

Urine samples from amantadine-treated CD2F1 transgenic mice overexpressing SSAT consistently demonstrated metabolism of the parent compound to acetylamantadine in all timed collection periods (FIG. 2). The acetylamantadine excreted in the urine as a cumulative percent of administered dose at 24 hr ranged between 2–6% with a mean of 4.5±1.0%.

In Vitro Studies of Spermidine Acetylation

Figure 3:
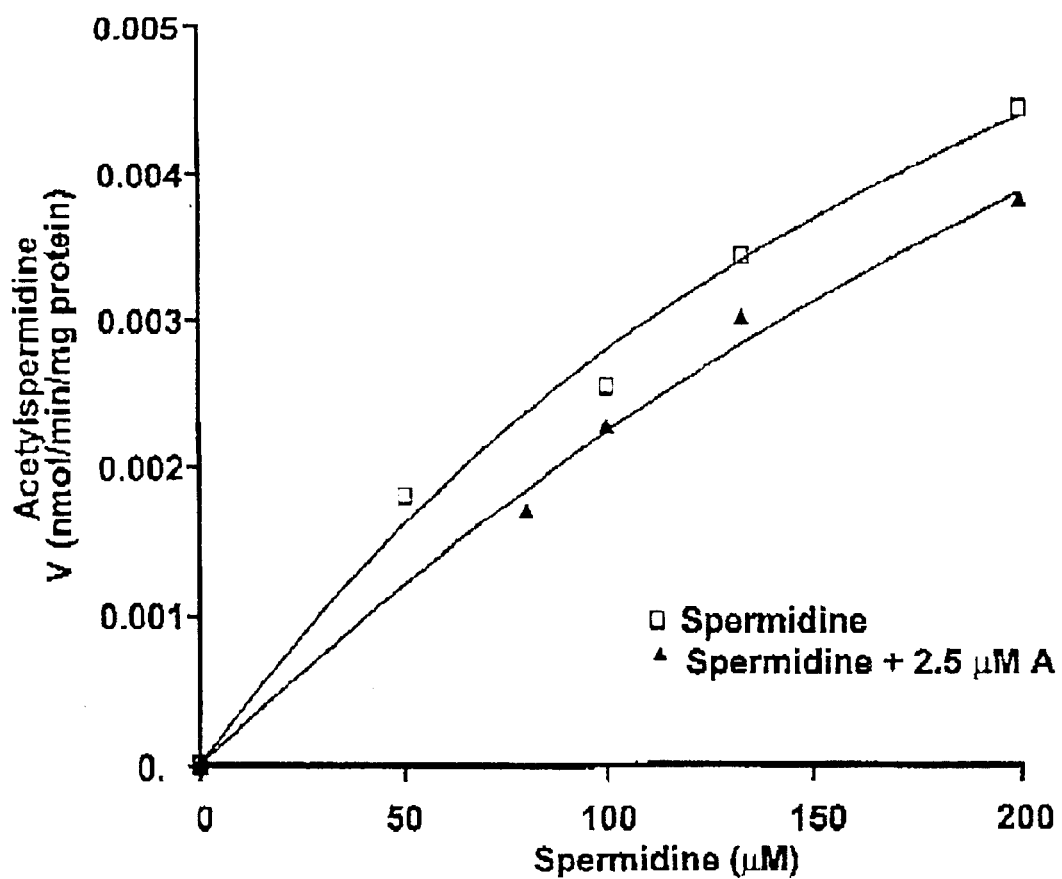
FIG. 3 is a representative plot of V vs. S demonstrating spermidine acetylation by transgenic mouse liver 100,000×g supernatant containing SSAT with apparent $K_m$=263 $\mu$M and $V_{max}$=0.010 nmol/min/mg protein ($r^2$=0.99). The addition of a therapeutic concentration (2.5 $\mu$M) of amantadine (A) causes inhibition of spermidine acetylation and an increase in the apparent $K_m$ to 542 $\mu$M and $V_{max}$ to 0.014 nmol/min/mg protein ($r^2$=0.99).

A representative non-linear velocity versus substrate concentration plot for spermidine acetylation by transgenic mouse liver 100,000×g supernatent containing SSAT is shown in FIG. 3. The kinetic parameters derived from these plots indicate an apparent $K_m$ of 267±46 $\mu$M and a $V_{max}$ of 0.009±0.002 nmol/min/mg protein (n=10, different mice). Using the non-transgenic mouse liver supernatant as a source of SSAT, spermidine acetylation was not detected.

Amantadine Inhibition Studies

Figure 4:
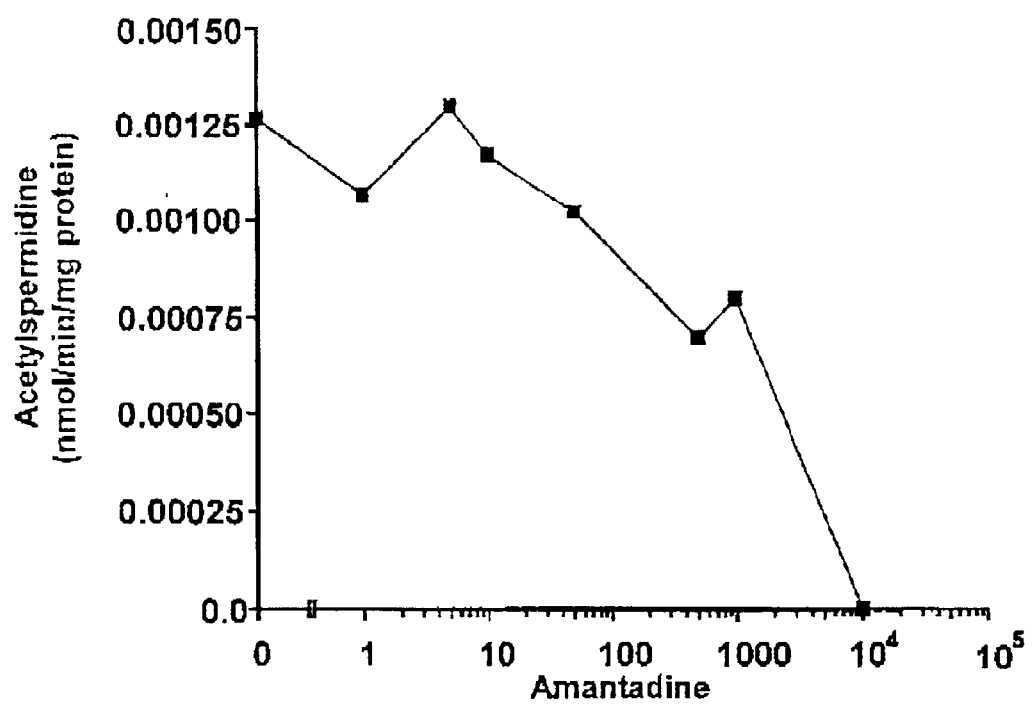
FIG. 4 is a representative plot for the inhibition of acetylspermidine production by increasing amantadine concentrations in the presence of 50 $\mu$M spermidine. Spermidine acetylation is completely inhibited by 10,000 $\mu$M amantadine.
Figure 5:
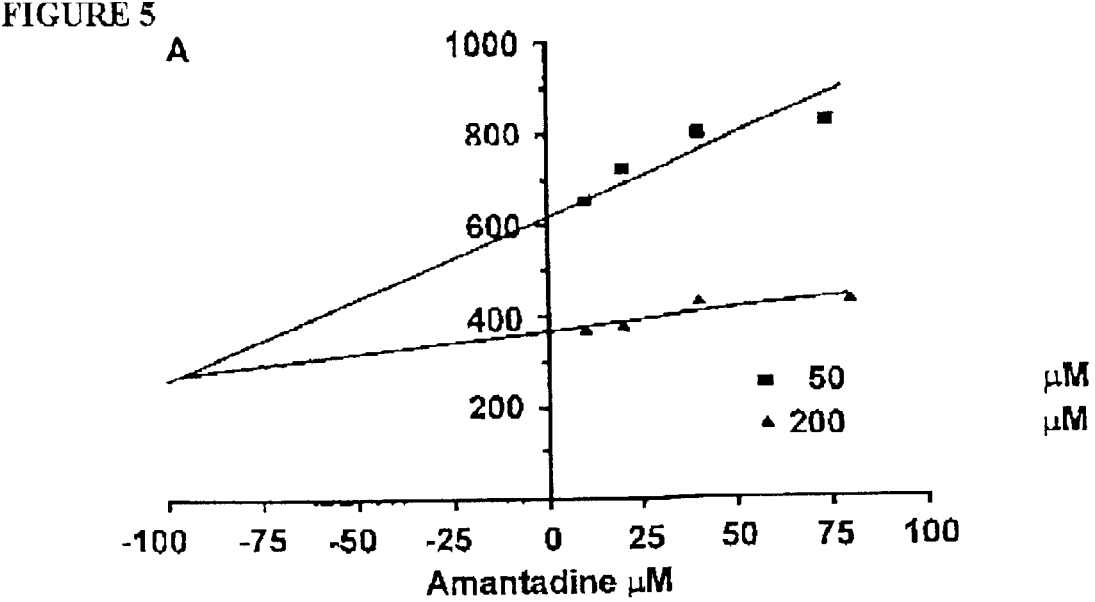
FIG. 5A is a representative Dixon plot of 1/v versus [I], showing the inhibition of acetylspermidine production by increasing amantadine [I] concentrations in the presence of 50 $\mu$M and 200 $\mu$M spermidine. The intersection of the two lines to left of y-axis and above the negative x-axis indicate the inhibition could be competitive or mixed inhibition.
FIG. 5B is a representative Cornish-Bowden plot S/v versus [I] of the same data as in FIG. 5A. The two parallel lines in the plot indicate competitive inhibition.
Figure 5:
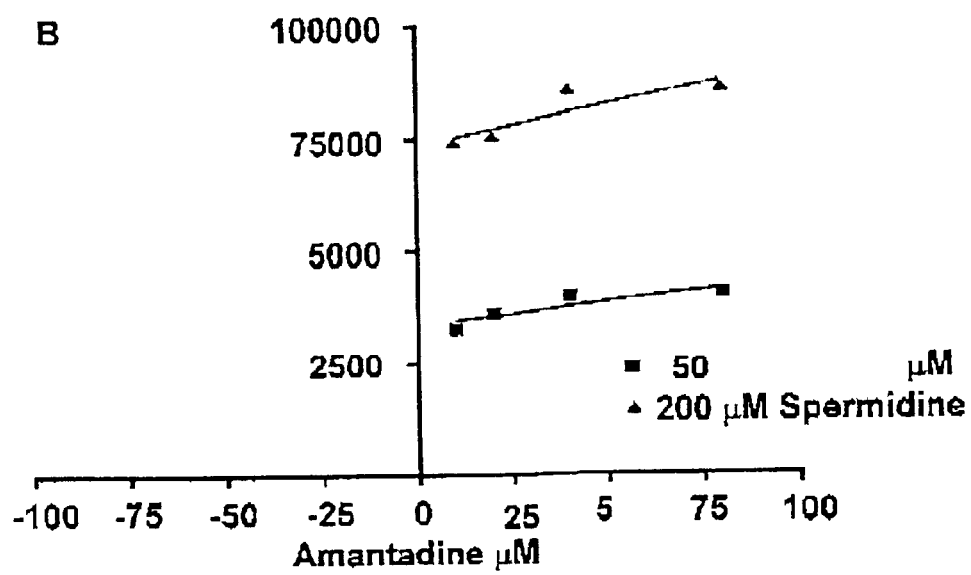

The ability of amantadine to inhibit spermidine acetylation by including it with spermidine incubations was evaluated. The addition of a therapeutic concentration of amantadine (2.5 $\mu$M) impeded the acetylation of spermidine, indicating it could serve as a substrate for the SSAT enzyme (FIG. 3). Subsequently, inhibition studies using fixed concentrations of spermidine (50 $\mu$M) and various concentrations of amantadine ranging from 1 to 10,000 $\mu$M were completed. A representative inhibition profile (FIG. 4) showed complete inhibition of the SSAT enzyme at 10,000 $\mu$M amantadine. Amantadine inhibition profiles were used to determine $IC_{50}$ values for spermidine acetylation. From the $IC_{50}$ values, the inhibitor dissociation constant ($K_i$) was calculated. Dixon and Cornish-Bowden analyses supported the interpretation that amantadine inhibition of spermidine acetylation was consistent with competitive inhibition (FIGS. 5A and 5B), and the use of $IC_{50}$ values to calculate the $K_i$. The apparent $IC_{50}$ and $K_i$ values were 935±191 $\mu$M and 738±157 $\mu$M respectively (n=13).

Amantadine Acetylation Studies

In vivo data showed that only transgenic male mice overexpressing SSAT excreted acetylamantadine in their urine. These mice contain at least 20 copies of the SSAT transgene, and have a level of SSAT activity in the liver that is 4 fold higher than seen in nontransgenic mouse liver (Pietila et al., 1997), strongly suggesting that SSAT is the enzyme catalyzing the acetylation of amantadine and possibly other primary amine- containing drugs and xenobiotics.

Furthermore, it was previously reported that Sprague-Dawley rats receiving the same therapeutic dose of amantadine did not excrete acetylamantadine in their urine (Goralski et al., 1999). These results are similar to studies showing that the non-transgenic mice of the same strain as the transgenic mice also failed to excrete acetylamantadine in their urine. These observations strongly suggest the need for increased levels of SSAT to be present before the acetylation of amantadine can occur. The percentage of the administered dose excreted by the transgenic mouse in their urine as acetylamantadine was similar to that shown in previous reports in humans (Bras et al., 1998; Koppel & Tenezer, 1985).

In vitro data using the transgenic mouse liver supernatant as the source of SSAT implicates it as the enzyme that acetylates amantadine, giving support to the in vivo observations. The data demonstrated that when amantadine was incubated with the transgenic mouse liver derived supernatant in the absence of spermidine, modest amounts of acetylamantadine were produced. This observation is consistent with low amounts of acetylation that occur in humans when they ingest amantadine (Bras et al., 1998; Koppel & Tenczer, 1985). These observations are further supported by in vitro data that showed that neither NAT1 nor NAT2 could explain amantadine acetylation (Bras et al., 1998), suggesting that amantadine is a specific substrate for SSAT. In contrast, the non-transgenic mice have inherently low levels of SSAT in their livers; in vitro experiments were performed and no acetylation of spermidine was detected. In addition, amantadine was not acetylated in other in vitro experiments using pig lung supernatant as the source of SSAT. In support of these findings, previous studies using non-induced and non-transgenic rat-derived liver supernatant revealed no detectable levels of acetylputrescine or acetylspermidine were produced (Blankenship & Walle, 1977; Seiler & al-Therib, 1974). Investigating amantadine acetylation led to the finding that SSAT is a previously unrecognized drug acetylating enzyme. The data suggest that amantadine is a novel drag substrate that can be used to evaluate and detect SSAT activity. Amantadine, being a specific substrate for SSAT, could be used to evaluate SSAT contribution to drug acetylation.

Drugs that contain the substituted diaminopropane structure that resembles part of spermidine, have been acetylated by SSAT. For in vitro experiments using human SSAT expressed in E. coli, Parry et al., demonstrated that the antitumor and immunosuppressive agent 1-deoxyspergualin, a metabolite of amifostine, the radioprotective and chemoprotective agent S-2-(3-aminopropylamino) ethanethiol (WR1065), and the spermine synthase inhibitor N-(n-butyl)-1,3-diaminopropane were acetylated by SSAT (Parry et al., 1995). However, besides these three drugs, no other studies have been reported that examined drugs that are not diaminopropane substituted as potential substrates for SSAT.

Further, in pathological states cellular polyamine levels are increased along with increased levels of $N^1$-acetylspermidine and polyamines excreted in the urine (Morgan, 1998; Russell, 1971; Suh et al., 1997). The increased levels of $N^1$-acetylspermidine observed in the urine of cancer patients suggests increased SSAT activity. The levels of SSAT activity in malignant tissues are greatly increased compared to normal tissues. Cancers with increased levels of $N^1$-acetylspermidine include gastric carcinoma, ovarian cancer, acute myelocytic leukemia, lymphoma, breast cancer, liver cancer, renal cancer, colorectal cancer, prostate cancer and others (Kingsnorth & Wallace, 1985; Pine et al., 1989; Sessa & Perin, 1991; Suh et al., 1997; Takenoshita et al., 1984). The increased expression and activity of SSAT seen in cancer cells prevents polyamines from reaching levels that would be toxic to the cell (Bettuzzi et al., 2000). The above observations support the interpretation that the increase in acetylation of NAT2 substrates observed in malignancy probably is due to increased levels of SSAT enzyme.

References

Andres, H. H. & Weber, W. W. (1986). N-acetylation pharmacogenetics. Michaelis-Menten constants for arylamine drugs as predictors of their N-acetylation rates in vivo. *Drug Metab Dispos*, 14, 382–5.

Bettuzzi, S., Davalli, P., Astancolle, S., Carani, C., Madeo, B., Tampieri, A., Corti, A., Saverio, B., Pierpaola, D., Serenella, A., Cesare, C., Bruno, M., Auro, T. & Arnaldo, C, (2000). Tumor progression is accompanied by significant changes in the levels of expression of polyamine metabolism regulatory genes and clusterin (sulfated glycoprotein 2) in human prostate cancer specimens. *Cancer Res*, 60, 28–34.

Blankenship, J. & Walle, T. (1977). Acetylation of spermidine and spermine by rat liver and kidney chromatin. *Arch Biochem Biophys*, 179, 235–42.

Bleidner, W. E., Harmon, J. B., Hewes, W. E., Lynes, T. E. & Hermann, E. C. (1965). Absorption, distribution and excretion of amantadine hydrochloride. *J Pharmacol Exp Ther*, 150, 484–90.

Bras, A. P., Hoff, H. R., Aoki, F. Y. & Sitar, D. S. (1998). Amantadine acetylation may be effected by acetyltransferases other than NAT1 or NAT2. *Can J Physiol Pharmacol*, 76, 701–6.

Casero, R. A. & Pegg, A. E. (1993). Spermidine/spermine N1-acetyltransferase-the turning point in polyamine metabolism. *Faseb J*, 7, 653–61.

Cohen, S. S. (1998). *A guide to the polyamines*. New York: Oxford University Press, Inc.

Davies, W. L., Grunert, R. R., Haff, R. F., McGahen, J. W., Neumayer, E. M., Paulshock, M., Watts, J. C., Wood, T. R., Hermann, E. C. & Hoffman, C. E. (1964). Antiviral activity of 1-adamantanamine (amantadine). *Science*, 144, 862–863.

Dupret, J. M. & Grant, D. M., (1992). Site-directed mutagenesis of recombinant human arylamine N-acetyltransferase expressed in *Escherichia coli*. Evidence for direct involvement of Cys68 in the catalytic mechanism of polymorphic human NAT2. *J Biol Chem*, 267,7381–5.

Fogel-Petrovic, M., Kramer, D. L., Ganis, B., Casero, K. A., Jr. & Porter, C. W. (1993). Cloning and sequence analysis of the gene acid cDNA encoding mouse spermidine/spermine N1-acetyltransferase—a gene uniquely regulated by polyamines and their analogs. *Biochim Biophys Acta*, 1216, 255–64.

Fogel-Petrovic, M., Kramer, D. L., Vujcic, S., Miller, J. McManis, J. S., Bergeron, R. J. & Porter, C. W. (1997). Structural basis for differential induction of spermidine/spermine N1-acetyltransferase activity by novel spermine analogs. *Mol Pharmacol*, 52, 69–74.

Goralski, K. B., Smyth, D. D, & Sitar, D. S. (1999). In vivo analysis of amantadine renal clearance in the uninephrectormized rat: functional significance of in vitro bicarbonate-dependent amantadine renal tubule transport. *J Pharmacol Exp Ther*, 290, 496–504.

Hickman, D., Palamanda, J. R., Unadkat, J. D. & Sim E. (1995). Enzyme kinetic properties of human recombinant arylamine N-acetyltransferase 2 allotypic variants expressed in *Escherichia coli*. *Biochem Pharmacol*, 50, 697–703.

Kingsnorth, A. N. & Wallace, H. M. (1985). Elevation of monoacetylated polyamines in human breast caners. *Eur J Cancer Clin Oncol*, 21, 1057–62.

Koppel, C. & Tenezer, J. (1985). A revision of the metabolic disposition of amantadine. *Biomed Mass Spectrom*, 12, 499–501.

Matsui, I. & Pegg, A. E. (1980). Effect of thioacetamide, growth hormone or partial hepatectomy on spermidine acetylase activity of rat liver cytosol. *Biochim Biophys Acta*, 633, 87–94.

Matsui, I. & Pegg, A. E (1980). Increase in acetylation of spermidine in rat liver extracts brought about by treatment with carbon tetrachloride. *Biochem Biophys Res Commun*, 92, 1009–15.

Matsui, I., Wiegand, L. & Pegg, A. E. (1981). Properties of spermidine N-acetyltransferase from livers of rats treated with carbon tetrachloride and its role in the conversion of spermidine into putrescine. *J Biol Chem*, 256, 2454–9.

Morgan, D. M. L. (1998). Polyamines. In *Polyamine Protocols*. ed. Morgan, D. M. L. pp. 3–30. Totowa: Humana Press.

Parry, L., Balana Fouce, R. & Pegg, A. E. (1995). Post-transcriptional regulation of the content of spermidine/spermine N1-acetyltransferase by N1N12-bis(ethyl) spermine. *Biochem J*, 305, 451–8.

Pegg, A. E., Seely, J. E., Poso, H., della Ragione, F. & Zagon, I. A. (1982). Polyamine biosynthesis and interconversion in rodent tissues. *Fed Proc*, 41, 3065–72.

Pegg, A. E., Stanley, B. A., Wiest, L. & Casero, R. A., Jr. (1992). Nucleotide sequence of hamster spermidine/spermine-N1-acetyltransferase cDNA. *Biochim Biophys Acta*, 1171, 106–8.

Pietila, M., Albonen, L., Halmekyto, M., Kanter, P., Janne, J. & Porter, C. W. (1997). Activation of polyamine catabolism profoundly alters tissue polyamine pools and affects hair growth and female fertility in transgenic mice overexpressing spermidine/spermine N1-acetyltransferase. *J Biol Chem*, 272, 18746–51.

Pine, M. J., Huber R. P & Pegg, A. E. (1989). Production of N1-acetyl spermidine by renal cell tumors. *J Urol*, 141, 651–5.

Russell, D. H. (1971). Increased polyamine concentrations in the urine of human cancer patients. *Nat New Biol*, 233, 144–5.

Seiler, N. (1987). Functions of polyamine acetylation. *Can J Physiol Pharmacol*, 65, 2024–35.

Seiler, N. & al-Therib, M. J. (1974). Acetyl-CoA: 1,4-diaminobutane N-acetyltransferase. Occurrence in vertebrate organs and subcellular localization. *Biochim Biophys Acta*, 354, 206–12.

Sessa, A. & Perin, A. (1991). Increased synthesis of N1-acetylspermidine in hepatic preneoplastic nodules and hepatomas. *Cancer Lett,* 56, 159–63.

Sitar, D. S., Hoff, H. R. & Aoki, F. Y, (1991). Amantadine acetylation in man is not predicted by acetylator phenotype. *Clin Pharmacol Ther,* 49, 156.

Suh, J. W., Lee, S. H., Chung, B. C. & Park, J. (1997). Urinary polyamine evaluation for effective diagnosis of various cancers. *J Chromatogr B Biomed Sci Appl,* 688, 179–86.

Takenoshita, S., Matsuzaki, S., Nakano, G., Kimura, H., Hoshi, H., Shoda, H. & Nakamura, T. (1984). Selective elevation of the N1-acetylspermidine level in human colorectal adenocarcinomas. *Cancer Res,* 44, 845–7.

Tannen, R. H. & Weber, W. W. (1979). Rodent models of the human isoniazid-acetylator polymorphism. *Drug Metab Dispos,* 7, 274–9.

Wang, Y., Devereux, W., Stewart, T. M. & Casero, R. A., Jr. (2001). Characterization of the interaction between the transcription factors human polyamine modulated factor (PMF-1) and NF-E2-related factor 2 (Nrf-2) in the transcriptional regulation of the spermidine/spermine N1-acetyltransferase (SSAT) gene. *Biochem J,* 355, 45–9.

Wang, Y., Devereux, W., Stewart, T. M. & Casero, R. A., Jr. (1999). Cloning and characterization of human polyamine-modulated factor-1, a transcriptional cofactor that regulates the transcription of the spermidine/spermine N(1)-acetyltransferase gene. *J Biol Chem,* 274, 22095–101.

Wang, Y., Xiao, L., Thiagalingam, A., Nelkin, B. D. & Casero, R. A., Jr. (1998). The identification of a cis-element and a trans-acting factor involved in the response to polyamines and polyamine analogues in the regulation of the human spermidine/spermine N1-acetyltransferase gene transcription. *J Biol Chem,* 273, 34623–30.

Xiao, L., Celano, P., Mank, A. R., Griffin, C., Jabs, E. W., Hawkins, A. L. & Casero, R. A., Jr. (1992). Structure of the human spermidine/spermine N1-acetyltransferase gene (exon/intron gene organization and localization to Xp22.1). *Biochem Biophys Res Commun,* 187, 1493–502.

What is claimed is:

1. A method for detecting spermine/spermidine $N^1$-acetyltransferase (SSAT) activity in a mammal comprising the steps of:

a) incubating an amount of amantadine in a maninial;

b) obtaining a tissue or cell or body fluid sample from the mammal; and c) detecting acetylamantadine in the sample; and d) correlating the presence of acetylamantadine to SSAT activity, wherein the presence of the acetylamantadine in the sample is indicative of SSAT activity in the mammal.

2. A method as in claim 1, wherein the amount of amantadine is equivalent to 1–4 mg/kg.

3. A method as in claim 1, wherein the sample is a blood or urine sample.

4. A method as in claim 1, wherein the urine sample is collected 2–24 hours post-incubating said amantadine in the mammal.

5. A method as in claim 1, wherein the urine sample is collected 8 hours post-incubating said amantadine in the mammal.

6. A method as in claim 1, wherein the step of correlating the presence of acetylamantadine in the sample comprises correlating the amount if acetylamantadine to a standard curve to determine the level of SSAT activity in the mammal.

7. A method as in claim 1, wherein the acetylamantadine level is detected by gas chromatography.

8. A method for assaying non-spermine/non-spermidine SSAT activity in a mammal, wherein the SSAT substrate is amantadine and acetylated form of the SSAT substrate is acetylamantadine comprising the steps of:

a) contacting a test sample obtained from the mammal with amantadine;

b) measuring the amount of acetylamantadine produced; and c) relating the amount of acetylamantadine produced to a level of SSAT activity.

9. The method of claim 8, wherein the sample is a homogenate of a liver tissue and the contacting step is performed at a pH of about 7.8.

10. The method of claim 8, wherein step a) comprises incubating the sample with the substrate for about 10 minutes at 37°C.

* * * * *

UNITED STATES PATENT AND TRADEMARK OFFICE
CERTIFICATE OF CORRECTION

PATENT NO. : 6,811,967 B2
DATED : November 2, 2004
INVENTOR(S) : Sitar et al.

It is certified that error appears in the above-identified patent and that said Letters Patent is hereby corrected as shown below:

Column 12,
Line 22, "correlating the amount if acetylamatadine to a standard" to
-- correlating the amount of acetylamantadine to a standard --

Signed and Sealed this

Fourteenth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,811,967 B2
DATED : November 2, 2004
INVENTOR(S) : Sitar et al.

It is certified that error appears in the above-identified patent and that said Letters Patent is hereby corrected as shown below:

<u>Title page,</u>
Item [75], Inventors, change "Daneil S. Sitar, Winnepeg (CA); to -- Daneil S. Sitar, Winnipeg (CA).

<u>Column 12,</u>
Line 1, change "a) incubating an amount of amantadine in a maninial;" to
-- a) incubating an amount of amantadine in a mammal. --.

Signed and Sealed this

Eleventh Day of October, 2005

JON W. DUDAS
*Director of the United States Patent and Trademark Office*

UNITED STATES PATENT AND TRADEMARK OFFICE
CERTIFICATE OF CORRECTION

PATENT NO. : 6,811,967 B2
APPLICATION NO. : 10/085051
DATED : November 2, 2004
INVENTOR(S) : Sitar et al.

It is certified that error appears in the above-identified patent and that said Letters Patent is hereby corrected as shown below:

Title Page
    Please change the inventor information as follows:
change:
(75) Inventors: Daneil S. Sitar, Winnepeg (CA);

to

(75) Inventors: Daniel S. Sitar, Winnipeg (CA)

Please change claim 1, column 12, line 1:
change:
a) incubating an amount of amantadine in a maninial;

to a) incubating an amount of amantadine in a mammal.

Signed and Sealed this

Second Day of October, 2007

JON W. DUDAS
*Director of the United States Patent and Trademark Office*